US00PP12220P2

(12) United States Plant Patent
Zary

(10) Patent No.: US PP12,220 P2
(45) Date of Patent: Nov. 27, 2001

(54) HYBRID TEA ROSE PLANT NAMED 'JACLEWT'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,225

(22) Filed: Dec. 6, 1999

(51) Int. Cl.[7] ..... A01H 5/00
(52) U.S. Cl. ..... Plt./130
(58) Field of Search ..... Plt./130, 137, 138, Plt./132

*Primary Examiner*—Howard J. Locker
(74) *Attorney, Agent, or Firm*—Klarquist Sparkman, LLP

(57) ABSTRACT

A hybrid tea rose plant having vigorous, upright growth and attractive lavender flowers on long stems having a strong, damask fragrance.

1 Drawing Sheet

The present invention relates to a new and distinct variety of rose plant of the hybrid tea class which was originated by me by crossing the variety AROpoiz (U.S. Plant Pat. No. 6,812), with the variety JACpurr (not patented).

The primary objective of this breeding was to produce a new rose variety having the deep rich fragrance, lavender flower color, upright growth and long stems of the female parent, combined with the dark foliage, fragrance and lack of thorns of the male parent. The objective was substantially achieved, along with other desirable improvements, as evidenced by the following unique combination of characteristics that are outstanding in the new variety and that distinguish it from its parents, as well as from all other varieties of which I am aware:

1. Strong damask fragrance;
2. Long stems;
3. Attractive lavender flowers;
4. Vigorous, upright growth; and
5. Small thorns.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:
*Seed parent.*—AROpoiz (U.S. Plant Pat. No. 6,812).
*Pollen parent.*—JACpurr (not patented).

Classification:
*Botanical.*—*Rosa hybrida.*
*Commercial.*—Hybrid tea.

FLOWER

Observations made from specimens grown in a garden environment at Somis, Calif. from March 1998 to August 1999.

Blooming habit: Continuous.

Bud:
*Size.*—About 1½ inches long when the petals start to unfurl.
*Form.*—The bud form is long; pointed ovoid.
*Color.*—When sepals first divide, bud color is Red-Purple Group 63D with petal edges of Red-Purple Group 63A. When half blown, the upper sides of the petals on their outer portions are Red-Purple Group 63D with the innermost ¼ of each petal White Group 155A. There is a thin edge on the petals of Red Group 63A; and the lower sides of the petals are Red-Purple Group 65D on their outer portions with the innermost ¼ of each petal White Group 155A.
*Sepals.*—Color: Green Group 138B. Surface texture: Covered in fine hairs. There are three normally appendaged sepals. There are two unappendaged sepals with serrated edges.
*Receptacle.*—Color: Yellow-Green Group 148B. Shape: Funnel. Size: Small (about ¼ inch × ⅛ inch). Surface: Smooth.
*Peduncle.*—Length: Short (about 1¼ to 1½ inches). Surface: Glandular. Color: Yellow-Green Group 148B, except when exposed to bright sun. Then it is Greyed-Red Group 178A. Strength: Stiff; erect.

Bloom:
*Size.*—Large. Average open size is four inches.
*Borne.*—Singly, and on basal breaks several together, in pyramidal clusters of five to seven blooms.
*Stems.*—Strength: Strong. Average length is about 18 to 22 inches.
*Form.*—When first open: High centered. Permanence: Flattens; outer petals curl back.
*Petalage.*—Number of petals under normal conditions: 35.
*Color.*—The upper sides of the petals are Red-Purple Group 63D on their outer part with the innermost ¼ of each petal White Group 155A. There is a thin edge of Red-Purple Group 63A on the petals. The reverse sides of the petals are Red-Purple Group 65D on their outer part with the innermost ¼ of each petal White Group 155A. The base of each petal has on both surfaces a small (⅛ inch×⅛ inch), Green-White Group 157D half moon at the point of attachment.

The major color on the upper side is Red-Purple Group 63D.

*Variegations.*—There are occasional Red-Purple Group 65D stripes, blotches or spots on the upper surface.

*Discoloration.*—The general tonality at the end of the first day: No change. At the end of the third day: No change. By day five there is a general fading, beginning on the outer petals, to Red-Purple Group 65D.

*Fragrance.*—Strong; heavy damask.

Petals:

*Texture.*—Thick.

*Shape.*—Deltoid.

*Form.*—Tips slightly recurved.

*Arrangement.*—Imbricated. Petaloids in the center are few and small (ranging from 0 to 7 in number), (from ¼ inch to ½ inch long and ⅛ inch to ¼ inch wide). Petaloid color is the same as the petals.

*Persistence.*—Petals drop off cleanly before drying.

*Lastingness.*—On the plant: Fair (about six or seven days). As a cut flower: Fair (about seven or eight days).

Reproductive parts:

*Anthers.*—Size: Medium. Quantity: Many. Color: Yellow-Orange Group 20C. Arrangement: Regular around styles.

*Filaments.*—Color: Green-White Group 157C.

*Pollen.*—Present.

*Styles.*—Color: Orange-White Group 159C.

*Stigmas.*—Color: Green-White Group 157C.

Plant:

*Form.*—Bush.

*Growth.*—Vigorous; upright; branching. At maturity, height is 5 to 5½ feet, width is 3½ feet.

Foliage: Number of leaflets on normal mid-stem leaves: five or seven.

*Size.*—Medium (4 to 4½ inches long×2½ to 3 inches wide).

*Quantity.*—Normal.

*Color.*—New foliage: Upper and lower surfaces: Greyed-Orange Group 178A. Old foliage: Upper surface: Green Group 139A. Lower surface: Green Group 139C.

Leaflets:

*Shape.*—Oval.

*Texture.*—Leathery; smooth.

*Edge.*—Serrated.

*Serration.*—Single; small.

*Petiole rachis.*—Color: Upper surface is Green Group 137B, lower surface is Yellow-Green Group 148C.

*Petiole underside.*—Smooth.

*Stipules.*—Medium (about ½ inch); bearded.

*Disease resistance.*—Susceptible to mildew and blackspot, resistant to rust under normal growing conditions.

Wood:

*New wood.*—Color: Yellow-Green Group 147C with Greyed-Red Group 178B on areas exposed to bright sun. Bark: Smooth.

*Old wood.*—Color: Yellow-Green Group 146C. Bark: Smooth.

Prickles:

*Quantity.*—On main canes from base: Ordinary. On laterals from main canes: Ordinary.

*Form.*—Short; hooked downward.

*Color when young.*—Greyed-Red Group 178C.

*Color when mature.*—Greyed-Yellow Group 161D.

Small prickles:

*Quantity.*—On main stalks: Few. On laterals: None.

*Color.*—Greyed-Yellow Group 161D.

I claim:

1. A new and distinct variety of rose plant of the hybrid tea class, substantially as herein shown and described, characterized particularly by its vigorous, upright growth and attractive lavender flowers on long stems having a strong, damask fragrance.

* * * * *

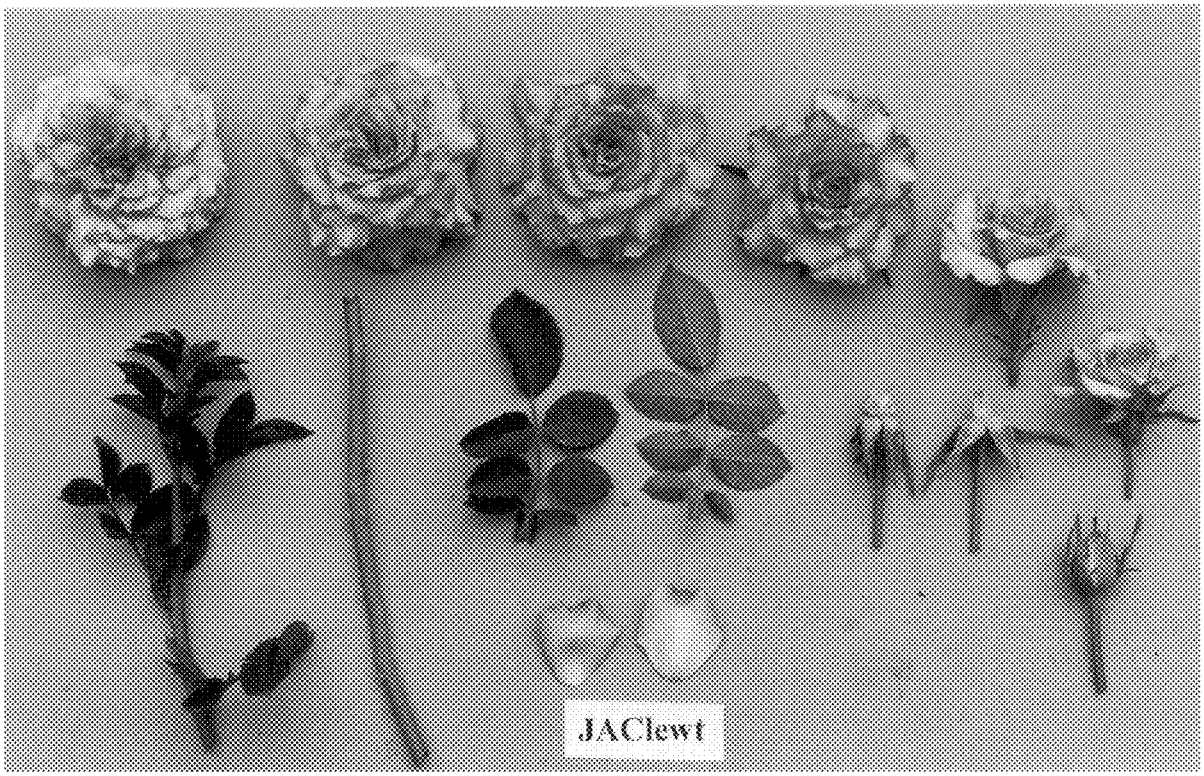
JAClewt